US00RE48906E

(19) United States
(12) Reissued Patent
Jung et al.

(10) Patent Number: US RE48,906 E
(45) Date of Reissued Patent: *Feb. 1, 2022

(54) FOAM HAVING IMPROVED FEELING DURING USE

(71) Applicant: AMOREPACIFIC CORPORATION, Seoul (KR)

(72) Inventors: Ha Jin Jung, Yongin-si (KR); Kyung Nam Kim, Yongin-si (KR); Jung Sun Choi, Yongin-si (KR); Kyung Ho Choi, Yongin-si (KR); Yeong Jin Choi, Yongin-si (KR)

(73) Assignee: Amorepacific Corporation, Seoul (KR)

( * ) Notice: This patent is subject to a terminal disclaimer.

(21) Appl. No.: 16/721,053

(22) Filed: Dec. 19, 2019

Related U.S. Patent Documents

Reissue of:
(64) Patent No.: 9,844,496
Issued: Dec. 19, 2017
Appl. No.: 14/391,088
PCT Filed: Apr. 12, 2013
PCT No.: PCT/KR2013/003101
§ 371 (c)(1),
(2) Date: Oct. 7, 2014
PCT Pub. No.: WO2013/154392
PCT Pub. Date: Oct. 17, 2013

(30) Foreign Application Priority Data

Apr. 12, 2012 (KR) ..... 10-2012-0038132
Apr. 11, 2013 (KR) ..... 10-2013-0039638

(51) Int. Cl.

| | |
|---|---|
| ***A61K 8/02*** | (2006.01) |
| ***A45D 34/00*** | (2006.01) |
| ***A45D 34/04*** | (2006.01) |
| ***A45D 40/26*** | (2006.01) |
| ***A61K 8/04*** | (2006.01) |
| ***A61K 8/81*** | (2006.01) |
| ***A61K 8/85*** | (2006.01) |
| ***A61K 8/86*** | (2006.01) |
| ***A61Q 17/04*** | (2006.01) |
| ***A61Q 19/00*** | (2006.01) |
| ***C08J 9/40*** | (2006.01) |

(52) U.S. Cl.
CPC ..... *A61K 8/0208* (2013.01); *A45D 34/00* (2013.01); *A45D 34/04* (2013.01); *A45D 40/26* (2013.01); *A61K 8/046* (2013.01); *A61K 8/8123* (2013.01); *A61K 8/8194* (2013.01); *A61K 8/85* (2013.01); *A61K 8/86* (2013.01); *A61Q 17/04* (2013.01); *A61Q 19/00* (2013.01); *C08J 9/40* (2013.01); *A45D 2200/1018* (2013.01); *A45D 2200/1036* (2013.01); *A61K 2800/87* (2013.01); *C08J 2201/036* (2013.01); *C08J 2307/00* (2013.01); *C08J 2309/02* (2013.01); *C08J 2309/06* (2013.01); *C08J 2323/06* (2013.01); *C08J 2327/06* (2013.01); *C08J 2331/04* (2013.01); *C08J 2371/00* (2013.01)

(58) Field of Classification Search
CPC .... A61K 8/8194; A61K 8/8123; A61K 8/046; A61K 8/0208; A61K 8/85; A61K 8/86; A61K 2800/87; A45D 34/04; A45D 34/00; A45D 40/26; A45D 2200/1036; A45D 2200/1018; A61Q 19/00; A61Q 17/04; C08J 9/40; C08J 2327/06; C08J 2201/036; C08J 2371/00; C08J 2323/06; C08J 2309/06; C08J 2309/02; C08J 2331/04; C08J 2307/00
See application file for complete search history.

(56) References Cited

U.S. PATENT DOCUMENTS

| | | | |
|---|---|---|---|
| 1,851,462 | A | 10/1932 | Steller |
| 2,204,203 | A | 6/1940 | Zimmerman |
| 2,764,565 | A | 9/1956 | Hoppe et al. |
| 3,133,309 | A | 5/1964 | Miles |
| 3,171,820 | A | 3/1965 | Volz |
| 3,463,745 | A | 8/1969 | Hofrichter et al. |
| 3,465,759 | A | 9/1969 | Haefele |
| 3,475,525 | A | 10/1969 | Peters |
| 3,748,288 | A | 7/1973 | Winkler et al. |
| 3,799,898 | A | 3/1974 | Lamplugh et al. |
| 3,949,137 | A | 4/1976 | Akrongold et al. |
| 4,130,121 | A | 12/1978 | Wetzel |
| 4,165,815 | A | 8/1979 | Vetter |
| 4,259,452 | A | 3/1981 | Yukuta et al. |
| 4,271,272 | A | 6/1981 | Stickman et al. |
| 4,309,509 | A | 1/1982 | Wood |
| 4,323,656 | A | 4/1982 | Strickman et al. |
| 4,344,930 | A | 8/1982 | MacRae et al. |
| 4,374,935 | A | 2/1983 | Decker et al. |

(Continued)

FOREIGN PATENT DOCUMENTS

| | | | |
|---|---|---|---|
| BE | 875638 | | 8/1979 |
| CA | 2900091 | * | 9/2009 |

(Continued)

OTHER PUBLICATIONS

Writen Opinion for International Application No. PCT/KR2013/003101 dated Jul. 3, 2013.

(Continued)

*Primary Examiner* — Norca L. Torres Velazquez
(74) *Attorney, Agent, or Firm* — Rothwell, Figg, Ersnt & Manbeck, P.C.

(57) ABSTRACT

The present invention relates to a foam made of a specific material having superior properties and to cosmetics comprising said foam.

10 Claims, 1 Drawing Sheet

(56) References Cited

U.S. PATENT DOCUMENTS

| | | | | |
|---|---|---|---|---|
| 4,427,798 | A | 1/1984 | Konig et al. | |
| 4,440,181 | A | 4/1984 | Scherer | |
| 4,537,912 | A | 8/1985 | Griswold | |
| 4,594,835 | A | 6/1986 | Gray | |
| 4,656,196 | A | 4/1987 | Kelly et al. | |
| 4,706,693 | A | 11/1987 | Spector | |
| 4,806,572 | A | 2/1989 | Kellett | |
| 4,906,672 | A | 3/1990 | Stone et al. | |
| 4,985,467 | A | 1/1991 | Kelly et al. | |
| 5,064,653 | A | 11/1991 | Sessions et al. | |
| 5,065,752 | A | 11/1991 | Sessions et al. | |
| 5,098,621 | A | 3/1992 | Hermann | |
| 5,296,518 | A | 3/1994 | Grasel et al. | |
| 5,486,167 | A | 1/1996 | Dragoo et al. | |
| 5,552,449 | A | 9/1996 | Sollers et al. | |
| 5,591,779 | A | 1/1997 | Bleys et al. | |
| 5,702,713 | A | 12/1997 | Joulia | |
| 5,762,946 | A | 6/1998 | Gueret | |
| 5,961,961 | A | 10/1999 | Dodkowski et al. | |
| 6,271,277 | B1 | 8/2001 | Bleys et al. | |
| 6,371,606 | B1 | 4/2002 | Free | |
| 6,391,233 | B1 | 5/2002 | Otani et al. | |
| 6,638,986 | B2 | 10/2003 | Falke et al. | |
| 6,706,775 | B2 | 3/2004 | Hermann et al. | |
| 7,427,412 | B1 | 9/2008 | Painter et al. | |
| 7,612,160 | B2 | 11/2009 | Nguyen-Kim et al. | |
| 7,811,021 | B2 * | 10/2010 | Gueret | A45D 33/02 401/196 |
| 8,367,083 | B2 * | 2/2013 | Barba | A61K 8/891 424/401 |
| 8,784,854 | B2 | 7/2014 | Choi et al. | |
| 9,532,637 | B2 | 1/2017 | Choi et al. | |
| 2002/0182245 | A1 | 12/2002 | Thomson | |
| 2004/0170670 | A1 | 9/2004 | Smith et al. | |
| 2005/0159500 | A1 | 7/2005 | Dreier et al. | |
| 2006/0210612 | A1 | 9/2006 | Simon | |
| 2006/0235100 | A1 | 10/2006 | Kaushiva et al. | |
| 2007/0189375 | A1 | 8/2007 | Thomson | |
| 2007/0277844 | A1 | 12/2007 | Gueret | |
| 2009/0018224 | A1 | 1/2009 | Niesten et al. | |
| 2009/0047495 | A1 | 2/2009 | Hubbs | |
| 2009/0197948 | A1 * | 8/2009 | Miyahara | A61K 8/90 514/474 |
| 2011/0014254 | A1 | 1/2011 | Choi et al. | |
| 2014/0023689 | A1 | 1/2014 | Kim et al. | |
| 2014/0341959 | A1 | 11/2014 | Choi et al. | |
| 2015/0078802 | A1 | 3/2015 | Choi et al. | |
| 2015/0117931 | A1 | 4/2015 | Jung et al. | |
| 2015/0118269 | A1 | 4/2015 | Choi et al. | |
| 2015/0196468 | A1 | 7/2015 | Kim et al. | |
| 2018/0360699 | A1 | 12/2018 | Jung et al. | |

FOREIGN PATENT DOCUMENTS

| | | | |
|---|---|---|---|
| CN | 101977587 | A | 2/2011 |
| DE | 2356460 | | 5/1974 |
| EP | 0528705 | | 2/1993 |
| EP | 0528705 | | 9/2000 |
| EP | 2425961 | A1 | 3/2012 |
| EP | 2837305 | | 2/2015 |
| EP | 2837374 | A1 | 2/2015 |
| GB | 1498363 | | 1/1978 |
| JP | S5755409 | | 9/1955 |
| JP | S6272732 | A | 4/1987 |
| JP | 1988196612 | | 12/1988 |
| JP | 1988199706 | | 12/1988 |
| JP | 02080257 | U | 6/1990 |
| JP | 3015878 | U | 9/1995 |
| JP | 07095964 | B2 | 10/1995 |
| JP | 08164019 | A | 6/1996 |
| JP | H08-228826 | A | 9/1996 |
| JP | 08266329 | A | 10/1996 |
| JP | 08325125 | A | 12/1996 |
| JP | H09-65921 | A | 3/1997 |
| JP | H9220118 | A | 8/1997 |
| JP | H09220118 | A | 8/1997 |
| JP | 3015878 | B2 | 3/2000 |
| JP | 200079016 | A | 3/2000 |
| JP | 3187673 | B2 | 5/2001 |
| JP | 2002-53640 | A | 2/2002 |
| JP | 2002255736 | A | 9/2002 |
| JP | 200312457 | | 1/2003 |
| JP | 2003012457 | A | 1/2003 |
| JP | 2003192826 | | 7/2003 |
| JP | 2003199425 | | 7/2003 |
| JP | 2003231197 | | 8/2003 |
| JP | 2003-289939 | A | 10/2003 |
| JP | 2004267277 | A | 9/2004 |
| JP | 2005-152186 | A | 6/2005 |
| JP | 2006241150 | A | 9/2006 |
| JP | 2007508086 | A | 4/2007 |
| JP | 2007330771 | A | 12/2007 |
| JP | 2008-043633 | A | 2/2008 |
| JP | 2009019008 | A | 1/2009 |
| JP | 2010-6294 | A | 1/2010 |
| JP | 4588357 | B2 | 12/2010 |
| JP | 2011132154 | | 7/2011 |
| JP | 2011132154 | A | 7/2011 |
| JP | 2015-512933 | A | 4/2015 |
| KR | 0131075 | | 11/1997 |
| KR | 1020000013194 | A | 3/2000 |
| KR | 100498655 | B1 | 7/2005 |
| KR | 1020090100643 | A | 9/2009 |
| KR | 1020100101278 | A | 9/2010 |
| KR | 1020100128163 | A | 12/2010 |
| KR | 1020130083852 | A | 7/2013 |
| KR | 10-2013-0116043 | | 10/2013 |
| KR | 1020130116043 | A | 10/2013 |
| KR | 1020130116044 | A | 10/2013 |
| KR | 1020130116182 | A | 10/2013 |
| KR | 1020130116205 | A | 10/2013 |
| KR | 1020140038880 | A | 3/2014 |
| KR | 1020150063196 | A | 6/2015 |
| WO | 9221448 | A1 | 12/1992 |
| WO | 9947127 | A1 | 9/1999 |
| WO | 0103538 | A1 | 1/2001 |
| WO | 2005039350 | A1 | 6/2005 |
| WO | 2008112139 | | 9/2008 |
| WO | 2009116817 | A2 | 9/2009 |
| WO | 2012128589 | A2 | 9/2012 |

OTHER PUBLICATIONS

Yang et al., "The preparation, properties and determinating of structure for open cell polyurethane foam", Journal of the Hebei Academy of Sciences, vol. 24, No. 3, pp. 59-61, 2007.

www.ifacemaker.com, a review of ALMAY Nearly Naked Foundation, May 29, 2003.

Alain Parfondry, "Polyurethane Technology & Applications", 15 pages, Nov. 2002.

Declaration of R. Randall Wickett, Petition for Inter Partes Review of U.S. Pat. No. 8,784,854 under U.S.C. §§311-319 and 37 C.F.R. §§42.1-.8, 42.100-,123, Jul. 27, 2018, 90 pages.

The HLB System, a time-saving guide to emulsifier selection, 22 pages, Mar. 1980.

Declaration of Robert Y. Lochhead, Ph.D, FRSC, Case IPR2018-01516, U.S. Pat. No. 8,784,854 B2, dated Nov. 30, 2018, 185 pages.

Petition for Inter Partes Review of U.S. Pat. No. 8,784,854 under U.S.C. §§311-319 and 37 C.F.R. §§42.1-.8, 42.100-.123, dated Aug. 6, 2018, 78 pages.

Patent Owner's Preliminary Response, Case IPR2018-01516, U.S. Pat. No. 8,784,854 B2, dated Nov. 30, 2018, 70 pages.

Decision: Denying Institution of Inter Partes Review 35 U.S.C. § 314(a), Case IPR2018-01516, U.S. Pat. No. 8,784,854 B2, Feb. 20, 2019, 29 pages.

Merquinsa, Polyurethane Types, Web site contents, pp. 1-8.

Meyer R. Rosen (ed.), Delivery System Handbook for Personal Care and Cosmetic Products, 2005, pp. 513-525.

Michael Szycher, Szycher's Handbook of Polyurethanes, 1999, p. 7-6.

(56) References Cited

OTHER PUBLICATIONS

Michael Szycher, Szycher's Handbook of Polyurethanes, 1999, pp. C-8, 21, and 24.
Mihail Ionescu, "Chemistry and Technology of Polyols for Polyurethanes", 2005, pp. 2-4, 49-50, 263, 538-540, 647, Rapra Technology Limited.
Polyurethane Technology & Applications, pp. 107-108.
Polyurethane Technology & Applications, pp. 311-330.
Polyurethane Technology & Applications, pp. 3-5, 89-90, 123, 125, 169-171, 223-226.
Seong-Mi Park, Researcher's Statement, COSMAX R&I Institute, Apr. 17, 2017, 1 page.
T. Thomson, Design and Applications of Hydrophilic Polyurethanes, 2000, pp. 1-9, Preface xi-xiii.
Test Result Sheet, "Stability Test of LLBB Cushion", Korea Conformity Laboratories, 2017, pp. 1-5.
Decision of Intellectual Property Trial and Appeal Board, 6th Department, Trial No. 2018Dang (decision reversing the original decision)76.
Decision of Intellectual Property Trial and Appeal Board, 7th Department, Trial No. 2018Jeong49.
Decision of Patent Court, 1st Dvision, Case No. 2016Heo8667 Invalidation of Registration (Patent).
Decision of Supreme Court, 1st Division, Case No. 2018Hu10596 Invalidation of Registration (Patent).
Kamicokrolock, "Review, Etude house Cushion Foundation", website contents, Mar. 14, 2015, 3 pages.
International Search Report with English Translation for International Application No. PCT/KR2015/003646 dated Jul. 21, 2015.
Japanese Office Action—Japanese Application No. 2016-561816 dated Jun. 12, 2018, citing references listed within.
Supplementary European Search Report for Application No. 15776533.0 dated Dec. 19, 2017.
Written Opinion for International Application No. PCT/KR2015/003646 dated Jul. 21, 2015.
Tony Abisaleh et al., "Polyurethane Technology & Applications", 18 pages.
Result report of reproduction experiments on Amorepacific's patent (No. 1257628), 2017, 21 pages.
Reticulated foam, Edited on Jun. 3, 2018, pp. 1-3, Retrieved from the Internet Jun. 15, 2018 <URL:https://en.wikipedia.org/wiki/Reticulated_foam>.
"Reticulated Polyurethane Foam", UFP Technologies, Retrieved from the Internet Jul. 8, 2016, pp. 1-3.
Reticulated Foam, Australian Foam Manufacturer, Joyce Foam Products, Retrieved from the Internet Nov. 10, 2016, <URL: http://www.joyce.com.au/foams/reticulatedfoam/>.
Seong-Mi Park, "Report on Stability Test of Sponge Impregnated with LLBB Cushion Cosmetic Composition", Cosmax R&I Institute, Apr. 19, 2017, pp. 1-5, Korea.
Sang-Beom Kim, "About Structure and Properties of Polyurethane Foam", Letter of Opinion, May 9, 2016, pp. 1-4.
Shimin Wu, et al., "Concise Dictionary of Fine Chemicals", Shenyang: Liaoning Science and Technology, (Jun. 1999), pp. 1-7.
Singaporean Written Opinion—Application No. 201209361-3 dated Sep. 9, 2013, citing previous filed references.
Taiwanese Office Action—TW Application No. 101109975 dated Jan. 13, 2014, citing previous filed references.
Taiwanese Office Action—TW Application No. 101109975 dated Feb. 10, 2014, citing previous filed references.
UFP Technologies—Reticulated Foam, (Copyright 2011), pp. 1-2, Retrieved from the Internet Sep. 2, 2015, <URL: http://www.ufpt.com/>.
Written Opinion for International Application No. PCT/KR2012/002141 dated Oct. 31, 2012.
"100% Open Cell Flexible Polyurethane Foams", FXI Reticulated Foams, Product Sheet, FXI, Inc., Retrieved from the Internet Nov. 22, 2016, 1 page, <URL: fxi.com>.
"BB Cushion Sponge is Melting", Posted on the Internet Feb. 4, 2015, <URL: http://www.todayhumor.co.kr/board/view.php?table=fashion&no=142195>.
Yoo, "Koean BB/CC Cushion Foundation Review", Aug. 16, 2013; http://www.liahyoo.com/2013/08/koran-bbcc-cushion-foundation.html.
Linde Group, "Plyurethane foaming",available online May 27, 2016.
Google date for Linde Group, "Polyurethane foaming", printed 2015.
TBK, "44 mm round tin pans", udated Aug. 2011: http://www.tkbtrading.com/item.php?item_id+1298&page=3.
"Filters for Fishkeeping", EMW filtertechnik, Product Brochure, Retrieved from the Internet Nov. 22, 2016, pp. 1-4, <URL: www.emw.de>.
"Nature Republic CC Cushion Pact Sponge Gets Melted!!", Posted on the Internet Feb. 5, 2015, <URL: http://blog.naver.com/clawsome/220263606984>.
"Reticulated (Open-Cell) & Non-Reticulated (Closed-Cell) Foam Swabs", Berkshire, Retrieved from the Internet Nov. 11, 2016, pp. 1-5, <URL: http://www.berkshire.com/shop/cleanroomcleaningswabs/foam.html>.
"Reticulated Foam" and "Open Cell Polyurethane Foam", Foam Engineers Limited, Retrieved from the Internet Jul. 8, 2016, pp. 1-2, <URL: http://www.foamengineers.co.uk/foammanufacturingsuppliers/reticulated-foam>.
"Reticulated Foam—Polyurethane-based foam with open cellular structure", Material Sample shop.com, Retrieved from the Internet Jul. 8, 2016, pp. 1-2, <URL: https://www.materialsampleshop.com/products/reticulatedfoampolyurethane-based-foam-with-open-cellular-structure>.
"Reticulated Open Cell Black Packaging Foam with Polyester Polyurethaner Material", Changzhou Dayetengfei Sponge Factory, Retrieved from the Internet Jul. 8, 2016, pp. 1-3, <URL: http://www.customizedfoam.com/sale-7566632-reticulatedopen-cellblack-packaging-foam-with-polyesterpolyurethaner-material.html>.
"Reticulated Polyurethane Foam", FXI Innovations, Retrieved from the Internet Nov. 11, 2016, pp. 1-3, <URL: http://fxi.com/foamtechnologies/processes/reticulation.php>.
"Reticulated Polyurethane Foam", UFP Technologies, Retrieved from the Internet Jul. 8, 2016, pp. 1-3, <URL: http://www.ufpt.com/materials/foam/reticulatedpolyurethane-foam.html>.
"Reticulated Polyurethane Foam: Quenching vs. Zapping", UFP Technologies, Retrieved from the Internet May 12, 2016, <URL: http://www.ufpt.com/resource-center/quenching-vs-zappingreticulated-polyurethane/>.
"Trend of Global Urethane Raw Materials and Products Market", KIET Overseas Industrial Information, Retrieved from the Internet Nov. 15, 2016, pp. 1-2, <URL: http://www.kiet.go.kr/servlet/isearch?mode=view&dataNo=43619>.
"Optimization Technology Support for Polyurethane Foam Production through Analysis of Correlations Between CellStructure and Properties", Ministry of Commerce, Industry and Energy, Sep. 30, 2003, pp. 8, 11 and 12, KR.
Canadian Office Action for corresponding Canadian Patent Application No. 2,804,298 dated Jan. 18, 2017, citing previously filed reference.
Canadian Office Action for corresponding Canadian Patent Application No. 2,804,298 dated Jan. 4, 2016, citing U.S. Pat. No. 3,133,309 and previously filed references.
Canadian Office Action for corresponding Canadian Patent Application No. 2,804,298 dated Sep. 12, 2016.
Canadian Office Action—Canadia Application No. 2804298 dated May 29, 2014.
Canadian Office Action—Canadia Application No. 2804298 dated Oct. 28, 2013.
Canadian Office Action—Canadian Application No. 2804298 dated May 6, 2015, citing U.S. Pat. No. 3,133,309.
Canadian Protest—Canadia Application No. 2804298 dated Mar. 30, 2015, citing U.S. Pat. No. 3,133,309.
Chang-Seop Oh, "Recent Prospect of Polyurethanes", ReSEAT Analysis Report, Sep. 10, 2004, pp. 1-7, KR.

(56) References Cited

OTHER PUBLICATIONS

Chinese Office Action for corresponding Chinese Patent Application No. 201280002267.3 dated Mar. 30, 2016.
Chinese Office Action—Chinese Application No. 201280002267.3 dated Dec. 3, 2014, citing previously filed references CN101977587 and JP4588357.
Chinese Office Action—Chinese Application No. 201280002267.3 dated Mar. 18, 2014, cited previously filed references CN101977587 and US20090047495.
Chinese Office Action—Chinese Application No. 201280002267.3 dated Sep. 8, 2015.
Chinese Patent Invalidation Request for corresponding Chinese Patent Application No. 201280002267.3.
European Office Action for corresponding European Patent Application No. 12759918.1 dated Mar. 1, 2016.
European Office Action—European Application No. 12759918.1 dated Aug. 11, 2015.
European Office Action—European Application No. 12759918.1 dated Jun. 18, 2015, citing U.S. Pat. No. 3,133,309.
European Office Action—European Application No. 12759918.1 dated Oct. 12, 2014.
European Search Report—EP Application No. 12759918.1 dated Jan. 22, 2014 from European Patent Office.
Extract from pp. 22-23 of Korean Patent Court Ruling (case No. 2016heo8667), 1 page.
Foaming Plant, Copyrights 2006, pp. 1-7, Retrieved from the Internet Jun. 25, 2018<URL:http://www.foamtecinll.com/index.php?shpage=vpage&vpage=fpprofile&lang=en&plan=FP>.
George Woods, "Flexible Polyurethane Foams", Chemistry and Technology, 1982, pp. 94-95, Applied Science Publishers Ltd., Essex, England.
Indian Office Action—Indian Application No. 10805/CHENP/2012 dated Jul. 14, 2017, citing references listed within.
INOAC—Reticulated PU Foam, Posted: Nov. 2009, p. 1, Retrieved from the Internet Sep. 2, 2015, <URL: http://www.inostech.com/>.
International Search Report for International Application No. PCT/KR2012/002141 dated Oct. 31, 2012.
Japanes Office Action—Japan Application No. 2014-008657 dated Jun. 18, 2015.
Japanese Office Action for corresponding Japanese Patent Application No. 2014-008657 dated Mar. 9, 2017, citing previously filed reference.
Japanese Office Action for corresponding Japanese Patent Application No-2014-008657 dated May 31, 2016, citing previously filed reference.
Japanese Office Action—Japan Application No. 2014-008557 dated Sep. 11, 2015.
Jong-Rae Park, "Catalytic Glycolysis of Polyether Urethane Foam Waste", Master's Thesis, Chonnam National University Graduate School, Department of Chemical Engineering, Aug. 1999, pp. 4-5, KR.
Korean Office Action with English Translation for Application No. 10-2011-0026466 dated Dec. 16, 2012.
Korean Office Action with English Translation for Application No. 10-2011-0026466 dated Jun. 6, 2012.
Malaysian Examination Report—Application No. PI2013000328 dated Apr. 3, 2015, citing previous filed references.
Notice of Allowance with English Translation for Application No. 10-2011-0026466 dated Apr. 17, 2013.
Notice of Opposition for EP 12759918.1 from European Patent Office issued on Jul. 19, 2018, citing the above references.
Open Cell Foam, The Foam Factory, Retrieved from the Internet Nov. 11, 2018, pp. 1-2, <URL: http://www.thefoamfactory.com/opencellfoam/filter.html>.
Polyurethane Foam, p. 1, <URL: http://web.archive.org/web/20090220164156/http://casefoam.com/Polyurethane-foam.htm>.
Polyurethane Foam, Retrieved from the Internet Nov. 15, 2016, pp. 1-2, <URL: https://web.archive.org/web/20021223120233/http://www.casefoam.com/Polyurethanefoam.htm>.
Written Opinion for International Application No. PCT/KR2013/003101 dated Jul. 3, 2013.
European Patent Office—European Application No. 13775492.5 dated May 24, 2016, citing above references.
Non-Final Office Action dated Apr. 21, 2016 in KCL0204US.
Non-final OA dated Jun. 7, 2017 for KCL0204USC.
Non-Final Office Action dated Nov. 25, 2016 in KCL0204US.
Japan Office Action Corresponding Patent Application No. JP 2015505648 dated Mar. 10, 2017, with Partial English Translation.
Translation of Decision of Refusal in Japanese Patent Application No. 2017-249768, dated Sep. 20, 2019, 6 pages.
Office Action issued in U.S. Appl. No. 16/722,222 dated Jul. 12, 2021, 54 pages.
Notice of Allowance issued in U.S. Appl. No. 16/841,014 dated Jul. 9, 2021, 20 pages.
International Search Report for International Application No. PCT/KR2013/003101 dated Jul. 3, 2013.

* cited by examiner

| | Comp. Ex. | Ex.1 | Ex.2 | Ex.3 | Ex.4 | Ex.5 |
|---|---|---|---|---|---|---|
| Images | | | | | | |
| Adhesion | 1 | 5 | 4 | 4 | 4 | 5 |
| Finish | 1 | 4 | 4 | 4 | 4 | 4 |
| Thin application | 2 | 5 | 4 | 4 | 4 | 5 |
| Soft applicability | 1 | 4 | 4 | 4 | 5 | 4 |
| Consistency | 1 | 4 | 4 | 4 | 4 | 5 |
| Uniformness | 1 | 4 | 4 | 4 | 4 | 5 |
| Softness | 1 | 4 | 4 | 4 | 5 | 4 |
| Smoothness | 2 | 4 | 5 | 4 | 4 | 5 |
| Improved skin texture | 1 | 4 | 4 | 5 | 4 | 4 |
| Silkiness | 2 | 4 | 4 | 5 | 4 | 4 |

FOAM HAVING IMPROVED FEELING DURING USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present disclosure relates to a foam having superior properties and a cosmetic comprising the same.

BACKGROUND ART

A cosmetic composition is commonly provided as stored in a vacuum container, a pump container or a glass container. However, these containers are inconvenient to carry. Recently, as the necessity of putting on or adjusting makeup outdoors increases, there is a need of a cosmetic composition that can be carried conveniently.

A compact-type container may be considered as a container capable of conveniently carrying a cosmetic composition. In order to hold a liquid cosmetic composition in the compact-type container, it should be considered whether the container is compatible with the carrier for cosmetic composition, whether the cosmetic composition can be effectively held in the carrier, whether the carrier can hold the cosmetic composition stably for a long time and whether an adequate amount of the cosmetic composition can be ejected from the carrier.

The inventors of the present disclosure have found out that a foam prepared from a specific material provides superior skin adhesion, finish, thin application, soft applicability, consistency, uniformness, softness, smoothness, improved skin texture or silkiness.

More specifically, the inventors of the present disclosure have confirmed that a foam prepared from a specific material provides superior skin adhesion, reduced skin roughness, improved skin texture or improved applicability.

BRIEF DESCRIPTION OF THE DRAWINGS

The FIGURE is a table showing the results of a panel evaluation on a scale of 1 (very poor) to 5 (very good) of several parameters relating to hand application of a cosmetic composition after storage each of the foams of Examples 1 to 5 compared to direct hand application of the cosmetic composition (Comp. Ex) and a photographic image of each foam.

DISCLOSURE

Technical Problem

The inventors of the present disclosure have found out that when an adequate amount of a cosmetic composition absorbed in a specific foam is taken with a hand and applied on the face, feeling of use is remarkably improved over when the cosmetic composition not absorbed in the foam is directly applied on the face. The present disclosure is directed to providing a foam providing improved feeling of use and a cosmetic comprising the same.

Technical Solution

In one general aspect, the present disclosure provides a foam for improving skin adhesion of a cosmetic composition, consisting of one or more material selected from a group consisting of acrylonitrile-butadiene rubber (NBR), styrene-butadiene rubber (SBR) and natural rubber (NR), and a cosmetic comprising the same.

In another general aspect, the present disclosure provides a foam for reducing skin roughness of a cosmetic composition, comprising one or more material selected from a group consisting of polyvinyl chloride, polyethylene and ethylene-vinyl acetate (EVA), and a cosmetic comprising the same.

In another general aspect, the present disclosure provides a foam for improving skin texture of a cosmetic composition, comprising one or more material selected from a group consisting of latex, silicone, film-type, styrene-isoprene-styrene (SIS), styrene-ethylene-butylene-styrene (SEBS), polyvinyl alcohol (PVA), silicone elastomer, nitrile, butyl, polyether and neoprene, and a cosmetic comprising the same.

Advantageous Effects

Foams of the present disclosure includes various materials so that provide improved skin adhesion, reduced skin roughness, improved skin texture or improved applicability and allow convenient use of a cosmetic composition with improved stability and portability. Since the foams have different uses, they may provide optimized feeling of use of cosmetics.

BEST MODE

As used herein, a "foam" refers to a polymer foamed by dry or wet foaming.

As used herein, "flocking" refers to a process of depositing very short fibers (flock) onto, e.g., a foam.

As used herein, "impregnation" means that a cosmetic composition is carried in a foam.

In an aspect, the present disclosure provides a foam for impregnating a cosmetic composition, comprising one or more material selected from a group consisting of acrylonitrile-butadiene rubber (NBR), styrene-butadiene rubber (SBR), natural rubber (NR), polyvinyl chloride, polyethylene, ethylene-vinyl acetate (EVA), latex, silicone, film-type, styrene-isoprene-styrene (SIS), styrene-ethylene-butylen-estyrene (SEBS), polyvinyl alcohol (PVA), silicone elastomer, nitrile, butyl, polyether and neoprene.

In an exemplary embodiment of the present disclosure, the foam may be flocked with cotton, cotton/acryl, cotton/acryl/polyester, cotton/rayon, acryl, polyamide, nylon, polyester, nylon/polyester or silk.

In another aspect, the present disclosure provides a foam for improving skin adhesion of a cosmetic composition, comprising a rubber, for example, one or more material selected from a group consisting of acrylonitrile-butadiene rubber (NBR), styrene-butadiene rubber (SBR) and natural rubber (NR).

"Improved skin adhesion" means that, when a cosmetic composition impregnated in the foam is applied to the skin, the cosmetic composition is tightly adhered to the surface of the skin without getting loose. The foam of the present disclosure is advantageous in that the cosmetic composition can be applied on the skin tightly, thinly and uniformly and thus can provide silkiness to the skin.

In another aspect, the present disclosure provides a cosmetic comprising: the foam; and a cosmetic composition impregnated in the foam.

In another aspect, the present disclosure provides a foam for reducing skin roughness of a cosmetic composition, comprising a vinyl, for example, one or more material selected from a group consisting of polyvinyl chloride, polyethylene and ethylene-vinyl acetate (EVA).

"Reduced skin roughness" means that, when a cosmetic composition impregnated in the foam is applied to the skin, the cosmetic composition makes the skin surface even by filling the unevenness of the skin. The roughness of the skin may be formed by pimples, scars or pores, but is not limited thereto.

In another aspect, the present disclosure provides a cosmetic comprising: the foam; and a cosmetic composition impregnated in the foam.

In another aspect, the present disclosure provides a foam for improving skin texture of a cosmetic composition, comprising a silicone, for example, one or more material selected from a group consisting of latex, silicone, film-type, styrene-isoprene-styrene (SIS), styrene-ethylene-butylene-styrene (SEBS), polyvinyl alcohol (PVA), silicone elastomer, nitrile, butyl, polyether and neoprene.

"Improving skin texture" means, when the skin tone is nonuniform due to intrinsic or extrinsic factors or when the skin texture is bumpy, making the skin tone uniform or making the skin texture smooth. The skin tone may be nonuniform due to pigmentation, aging, exposure to UV, etc., but is not limited thereto.

In another aspect, the present disclosure provides a cosmetic comprising: the foam; and a cosmetic composition impregnated in the foam.

In another aspect, the present disclosure provides a foam for improving skin applicability of a cosmetic composition, wherein the foam described above is flocked with cotton, cotton/acryl, cotton/acryl/polyester, cotton/rayon, acryl, polyamide, nylon, polyester, nylon/polyester or silk.

"Improved skin applicability" means that the cosmetic composition can be applied thinly and uniformly on the skin without scrubbing or coming off and, thus, a natural feeling of use is provided.

In another aspect, the present disclosure provides a cosmetic comprising: one or more of the foam; and a cosmetic composition impregnated in the foam.

In an exemplary embodiment of the present disclosure, the cosmetic composition may be in liquid or solid state. Specifically, the cosmetic composition may be solution, emulsion, gel, cream or suspension.

In an exemplary embodiment of the present disclosure, the cosmetic composition may be an aqueous dispersion, an oily dispersion, a water-in-oil (W/O) emulsion or an oil-in-water (O/W) emulsion.

In general, a cosmetic composition in liquid state is difficult to carry and store as compared to one in solid state. However, the cosmetic comprising the foam according to the present disclosure is advantageous in that even a cosmetic composition in liquid or cream state can be stored and carried stably and safely. If the cosmetic composition is in solid state, it can be comprised in the carrier (foam) to reduce instant change in physical properties due to heat or external impact. Further, since the carrier serves to fix the cosmetic composition, an adequate amount of the content can be ejected.

In an exemplary embodiment of the present disclosure, the cosmetic composition that may be comprised in the cosmetic may be an emulsion composition, specifically a water-in-oil (W/O) emulsion or an oil-in-water (O/W) emulsion, or a dispersion composition, specifically an oily dispersion or an aqueous dispersion.

In an exemplary embodiment of the present disclosure, the cosmetic composition that may be comprised in the cosmetic may be prepared into, for example, makeup primer, makeup base, liquid or solid foundation, concealer, lipstick, lip gloss, powder, lip liner, eyebrow, eye shadow, blusher (blusher), twin cake, sunscreen, lotion, cream, essence, etc., but is not limited thereto.

[In an exemplary embodiment of the present disclosure, the cosmetic impregnated in the foam may be applied to the skin using a hand or an applicator (e.g., puff).]

Hereinafter, the present disclosure will be described in detail through examples. However, the following examples are for illustrative purposes only and it will be apparent to those of ordinary skill in the art that the scope of the present disclosure is not limited by the examples.

Preparation Example

A cosmetic composition (emulsion) containing the components described in Table 1 was impregnated in foams of Examples 1-5.

TABLE 1

| Components | Contents (wt %) |
|---|---|
| Ozokerite | 0.1 |
| Dicaprylyl carbonate | 10.0 |
| Methylparaben | 0.1 |
| Octyl methoxycinnamate | 7.0 |
| Isoamyl p-methoxycinnamate | 2.0 |
| Disteardimonium hectorite | 0.2 |
| Decamethylcyclopentasiloxane | 16.0 |
| Sorbitan sesquioleate | 2.0 |
| Lautyl PEG/PPG-18/18 methicone | 1.5 |
| Poly(methyl methacrylate) | 5.0 |
| Titanium dioxide/aluminum hydroxide/stearic acid | 7.0 |
| Water | To 100 |
| Glycerine | 8.0 |
| Salt | 1.0 |
| Fragrance | 0.4 |
| Total | 100.0 |

Comparative Example

At room temperature, 0.5 g of the cosmetic composition was taken with a hand and applied onto the face.

Example 1

At room temperature, the cosmetic composition was impregnated in a foam prepared from acrylonitrile-butadiene rubber (NBR) and having a diameter of 48 mm and a thickness of 50 mm. After waiting for 2 hours until stabilization, 0.5 g of the cosmetic composition was ejected from the foam by pressing with a hand and applied onto the face.

Example 2

At room temperature, the cosmetic composition was impregnated in a foam prepared from polyvinyl chloride and having a diameter of 48 mm and a thickness of 50 mm. After waiting for 2 hours until stabilization, 0.5 g of the cosmetic composition was ejected from the foam by pressing with a hand and applied onto the face.

Example 3

At room temperature, the cosmetic composition was impregnated in a foam prepared from latex and having a diameter of 48 mm and a thickness of 50 mm. After waiting for 2 hours until stabilization, 0.5 g of the cosmetic composition was ejected from the foam by pressing with a hand and applied onto the face.

Example 4

At room temperature, the cosmetic composition was impregnated in a foam prepared from polyether and flocked with polyester and having a diameter of 48 mm and a thickness of 50 mm. After waiting for 2 hours until stabilization, 0.5 g of the cosmetic composition was ejected from the foam by pressing with a hand and applied onto the face.

Example 5

At room temperature, the cosmetic composition was impregnated in a foam prepared from polyether and having a diameter of 48 mm and a thickness of 50 mm. After waiting for 2 hours until stabilization, 0.5 g of the cosmetic composition was ejected from the foam by pressing with a hand and applied onto the face.

Test Example

Evaluation was performed by 5 professional women panels who were aged 24-35 years, had makeup experiences for at least 2 years and wore makeup at least 5 times a week. They were asked to evaluate each test item with 5-point standards (1: very poor, 2: poor, 3: moderate, 4: good, 5: very good). The result is given in Table 2.

'Adhesion' is indicative of skin adhesion. 'Finish' is indicative of stickiness or other residual feeling after application to the skin. 'Thin application' is indicative of thickness of makeup after application to the skin. 'Soft applicability' is indicative of applicability to the skin. 'Consistency' is indicative of consistency of makeup after application to the skin. 'Uniformness' is indicative of reduced partial lumping after application. 'Softness' is indicative of baby face-like softness after application. 'Smoothness' is indicative of reduced skin roughness. 'Improved skin texture' is indicative of mending of skin tone or providing of smooth skin texture. 'Silkiness' is indicative of smooth application to the skin.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A cosmetic, comprising a carrier foam comprising one or more materials selected from the group consisting of acrylonitrile-butadiene rubber (NBR), polyvinyl chloride, latex, and polyether, and impregnated therein a cosmetic composition comprising octyl methoxycinnamate, wherein the carrier foam stores the cosmetic composition.

2. The cosmetic according to claim 1, wherein the foam is flocked with cotton, cotton/acryl, cotton/acryl/polyester, cotton/rayon, acryl, polyamide, nylon, polyester, nylon/polyester or silk.

3. The cosmetic according to claim 1, wherein the one or more material is acrylonitrile-butadiene rubber (NBR).

4. The cosmetic according to claim 3, wherein the foam is flocked with cotton, cotton/acryl, cotton/acryl/polyester, cotton/rayon, acryl, polyamide, nylon, polyester, nylon/polyester or silk.

5. The cosmetic of claim 1, wherein the cosmetic composition comprises Ozokerite, Dicaprylyl carbonate, Methylparaben, Isoamyl p-methoxycinnamate, Disteardimonium hectorite, Decamethylcyclopentasiloxane, Sorbitan sesquioleate, Lauryl PEG/PPG-18/18 methicone, Poly(methyl methacrylate), Titanium dioxide/aluminum hydroxide/stearic acid, Water, Glycerine, Salt, and Fragrance.

6. The cosmetic of claim 1, wherein the cosmetic composition further comprises Isoamyl p-methoxycinnamate.

7. The cosmetic of claim 6, further comprising Decamethylcyclopentasiloxane.

8. The cosmetic of claim 7, further comprising Ozokerite, Dicaprylyl carbonate, Methylparaben, Disteardimonium hectorite, Sorbitan sesquioleate, Lauryl PEG/PPG-18/18 methicone, Poly(methyl methacrylate), Titanium dioxide/aluminum hydroxide/stearic acid, Water, Glycerine, Salt, and Fragrance.

9. The cosmetic according to claim 1, wherein the cosmetic composition is in liquid or solid state.

10. The cosmetic according to claim 1, wherein the cosmetic composition is an aqueous dispersion, an oily dispersion, a water-in-oil (W/O) emulsion or an oil-in-water (O/W) emulsion.

[11. The cosmetic of claim 1, further comprising an applicator.]

* * * * *